United States Patent [19]

Renault

[11] Patent Number: 4,482,711

[45] Date of Patent: Nov. 13, 1984

[54] PROCESS FOR THE PREPARATION OF N,N-DIMETHYL-10-[1-AZA-[2,2,2]-BICYCLO-3-OCTYL]-10H-2-PHENOTHIAZINE SULPHONAMIDE

[75] Inventor: Christian Renault, Taverny, France

[73] Assignee: Pharmindustrie, Gennevilliers, France

[21] Appl. No.: 404,116

[22] Filed: Aug. 2, 1982

Related U.S. Application Data

[63] Continuation of Ser. No. 249,993, Mar. 30, 1981, abandoned.

[30] Foreign Application Priority Data

Jan. 13, 1981 [FR] France ................. 81 00442

[51] Int. Cl.$^3$ ........................................... C07D 417/00
[52] U.S. Cl. ................................................. 544/42
[58] Field of Search ........................... 544/42; 546/133

[56] References Cited

U.S. PATENT DOCUMENTS 2,909,521 10/1959 Jacob et al. ........................... 544/42
3,534,053 10/1970 Sallay et al. ........................ 546/133
3,563,995 2/1971 Wellings ............................... 546/133
3,987,042 10/1976 Gueremy et al. ................... 424/247

FOREIGN PATENT DOCUMENTS 611405 12/1960 Canada ................................. 544/42
1246742 8/1967 Fed. Rep. of Germany ........ 544/42
1492157 11/1977 United Kingdom ................. 544/42

OTHER PUBLICATIONS

Theilheimer, Synthetic Methods Org. Chem. 22 p. 230 No. 531 (1968).

Primary Examiner—Ethel G. Love
Attorney, Agent, or Firm—Beveridge, DeGrandi & Kline

[57] ABSTRACT

Process for the preparation of N,N-dimethyl-10[1-aza-[2,2,2]-bicyclo-3-octyl]-10H-2-phenothiazine sulphonamide, usable as a gastric secretion inhibitor, characterized in that N,N-dimethyl-3-[(1-aza-[2,2,2]-bicyclo-3-octyl)amino]-4-[(2-bromophenyl)thio] benzene sulphonamide is cyclized in the presence of an alkali metal amide.

15 Claims, No Drawings

PROCESS FOR THE PREPARATION OF N,N-DIMETHYL-10-[1-AZA-[2,2,2]-BICYCLO-3-OCTYL]-10H-2-PHENOTHIAZINE SULPHONAMIDE

This is a continuation of application Ser. No. 249,993 filed Mar. 30, 1981, now abandoned.

The present invention relates to a new process for the preparation of N,N-dimethyl-10-[1-aza-[2,2,2]-bicyclo-3-octyl]-10H-2-phenothiazine sulphonamide, of the formula:

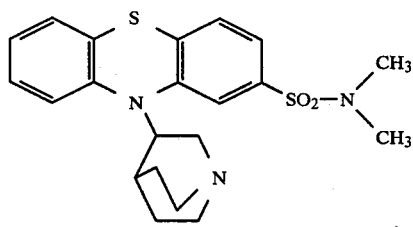

The compound of formula (I) is a known compound which is especially usable as a gastric secretion inhibitor and whose preparation is described in French certificate of addition 2,318,638.

According to this certificate of addition, the compound of formula (I) is obtained by condensing, in an inert solvent comprising an aromatic hydrocarbon and a dipolar aprotic solvent, the benzene sulphonic ester of 1-aza-[2,2,2]-bicyclo-3-octanol of the formula:

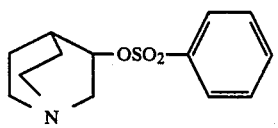

with a metallic derivative of N,N-dimethyl-2-phenothiazine sulphonamide of the formula:

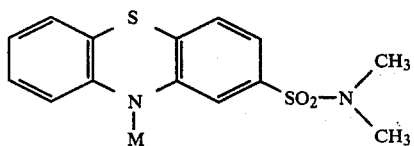

in which M denotes an alkali metal, in particular sodium. The yield in compound of formula (I), calculated relative to the starting products (II) and (III), is 40%.

The compound of formula (II) is itself prepared, in two stages, by reducing 1-aza-[2,2,2]-bicyclo-3-octanone to 1-aza-[2,2,2]-bicyclo-3-octanol (cf. C. A. GROB ET AL., Helv. Chim. Acta, 1957, 40, 2170) and acting, on the latter, benzene sulphonyl chloride (cf. E. E. Mikhlina et al., J. GEN. CHEM. U.R.S.S., 1960, 30, 2953). The yield in compound of formula (II), calculated relative to 1-aza-[2,2,2]-bicyclo-3-octanone, is 57.6%.

The compound of formula (III) is obtained by acting, in an inert solvent such as an aromatic hydrocarbon, an alkali metal hydride or amide on N,N-dimethyl-2-phenothiazine sulphonamide which is itself obtained, with a yield of 71%, by cyclizing N,N-dimethyl-3-amino-4-[(2-bromophenyl)thio] benzene sulphonamide (cf. V. V. Shavyrina et al., Med. Prom. U.R.S.S., 1966, 20,15).

On the whole, when the process described in French certificate of addition No. 2,318,638 is used, five stages are necessary to synthesize the compound of formula (I) from 1-aza-[2,2,2]-bicyclo-3-octanone and N,N-dimethyl-3-amino-4-[(2-bromophenyl)thio] benzene sulphonamide and the yield in compound (I) is only 23% relative to 1-aza-[2,2,2]-bicyclo-3-octanone and 28% relative to N,N-dimethyl-3-amino-4-[(2-bromophenyl)thio] benzene sulphonamide.

A new process has now been found, according to the present invention, for the preparation of the compound of formula (I), which allows this compound to be synthesized from 1-aza-[2,2,2]-bicyclo-3-octanone and from N,N-dimethyl-3-amino-4-[(2-bromophenyl)thio] benzene sulphonamide in three stages instead of five and allows the yield in compound (I) to be increased considerably relative to 1-aza-[2,2,2]-bicyclo-3-octanone and N,N-dimethyl-3-amino-4-[(2-bromophenyl)thio] benzene sulphonamide.

This new process comprises cyclizing the compound of formula (IV) below, according to the reaction diagram:

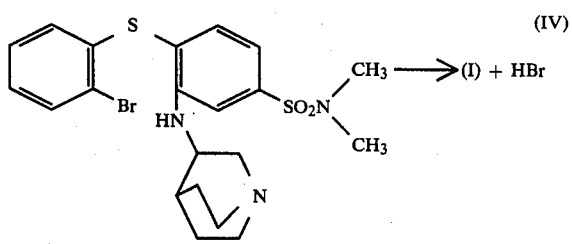

In formula (IV), the bromine atom can be replaced by a chlorine atom, in which case the reaction yields compound (I) and HCl.

The cyclization reaction is effected in the presence of an alkali metal amide, in particular sodium amide. Examples of other suitable alkali metal amides include lithium amide and potassium amide. The cyclization reaction may be effected either in liquid ammonia, at a temperature of between −40° C. and the boiling temperature of liquid ammonia under atmospheric pressure, or in an aprotic solvent in the presence of an alcohol or not in the presence of an alcohol, at a temperature of between 20° C. and the boiling temperature of the solvent. Examples of suitable aprotic solvents include tetrahydrofuran, 1,2-dimethoxyethane, hexamethylphosphorous triamide or their mixtures. In the case of the variant in aprotic solvent medium, the operation is preferably conducted in the presence of an alcohol, such as for example tertiobutanol, monoethyl ether of diethylene glycol, or tert-amyl alcohol, and at a temperature of about 20° C.

The compound of formula(IV) or N,N-dimethyl-3-[(1-aza-[2,2,2]-bicyclo-3-octyl)amino]-4-[(2-bromophenyl)thio] benzene sulphonamide may be prepared by condensing 1-aza-[2,2,2]-bicyclo-3-octanone with N,N-dimethyl-3-amino-4-[(2-bromophenyl)thio] benzene sulphonamide of formula (V) according to the following reaction diagram:

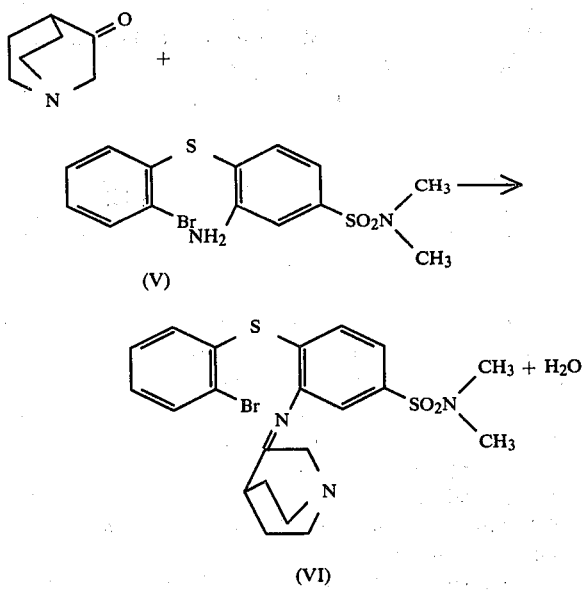

and reducing the imine of formula (VI) thus formed.

For the condensation reaction, the 1-aza-[2,2,2]-bicyclo-3-octanone is used in the free base state or in the state of a salt of the base (hydrochloride, for example). The condensation reaction is effected either in an aromatic hydrocarbon (such as for example xylene, toluene, benzene) in the presence of a protonic acid (for example, mineral acid such as sulfuric acid or organic acid such as acetic acid or p-toluene sulphonic acid) and at the boiling temperature of the medium (this allows the water, formed by azeotropic distillation, to be eliminated), or in an inert solvent (such as for example aromatic hydrocarbon such as toluene, benzene, xylene, or ether such as tetrahydrofuran, or halogenated solvent such as chloroform), in the presence of a dehydration agent (for example, titanium tetrachloride) and at a temperature of between −5° C. and +10° C.

The imine of formula (VI) may be reduced by means of an alkali metal borohydride (for example, sodium borohydride), in an alcohol such as ethanol or by means of lithium aluminohydride in an inert solvent such as tetrahydrofuran and at a temperature of between 0° C. and 40° C. To effect the reduction reaction, it is not necessary to isolate, in a pure state, the imine (VI) formed in the previous condensation reaction.

The compound of formula (I), formed by cyclizing the compound of formula (IV), is isolated in a pure state from the reaction mixtures by conventional methods, either physical methods (evaporation, extraction by means of a solvent, distillation, crystallization, chromatography, etc.) or chemical methods (formation of salt and regeneration of the base, etc.).

The following examples illustrate the invention without limiting it.

EXAMPLE 1

Preparation of
N,N-dimethyl-3-[(1-aza-[2,2,2]-bicyclo-3-octyl)amino]-4-[(2-bromophenyl)thio)] benzene sulphonamide.

Introduced into 150 ml of chloroform, placed under a dry nitrogen atmosphere, are 4.85 g of 1-aza-[2,2,2]-bicyclo-3-octanone hydrochloride, 11.61 g of N,N-dimethyl-3-amino-4-[(2-bromophenyl)thio] benzene sulphonamide and 25 ml of triethylamine. The mixture is stirred and the obtained solution is cooled to −5° C., with continuous stirring. Within the space of 90 minutes, a solution of 3.3 ml of titanium tetrachloride in 15 ml of chloroform is added. Stirring is continued at −5° C. for 20 hours, then, whilst keeping the temperature below 0° C., 10 ml of absolute ethanol are added.

The chloroform is evaporated under reduced pressure and the residue is dissolved in 150 ml of absolute ethanol. 7.5 g of sodium hydroxide in pellets, then 2.3 g of sodium borohydride are added. Stirring is effected for 20 hours at ambient temperature. The mixture is filtered, the insoluble matter is washed with 4 times 50 ml of absolute ethanol, the filtrate and the washing solutions are combined and are evaporated under reduced pressure.

The residue is taken up by 50 ml of water and 50 ml of toluene. The toluene phase is separated by decantation and the aqueous phase is extracted by 2 times 50 ml of toluene. The collected toluene phases are extracted by 50 ml of an aqueous N solution of methane sulphonic acid and 4 times 25 ml of water. The acidic aqueous phase is washed with two times 50 ml of diethyl oxide, brought to pH≃8 by the addition of a concentrated solution of ammonia and the oil which salts out is extracted with 4 times 50 ml of toluene. The toluene phases are dried on anhydrous magnesium sulphate, filtered and evaporated under reduced pressure. Thus, 10.4 g are obtained of N,N-dimethyl-3-[(1-aza-[2,2,2]-bicyclo-3-octyl)amino]-4-[(2-bromophenyl)thio] benzene sulphonamide, which melts at 129°–130° C. The yield in this latter product, calculated relative to the initial 1-aza-[2,2,2]-bicyclo-3-octanone, is approximately 70%.

EXAMPLE 2

Preparation of
N,N-dimethyl-3-[(1-aza-[2,2,2]-bicyclo-3-octyl)amino]-4-[(2-bromophenyl)thio] benzene sulphonamide A mixture of 70 ml of xylene, 3.87 g of N,N-dimethyl-3-amino-4-[(2-bromophenyl)thio] benzene sulphonamide, 1.25 g of 1-aza-[2,2,2]-bicyclo-3-octanone and 0.19 g of p-toluene sulphonic acid is heated for 50 hours up to reflux, the water which is formed by azeotropic distillation being eliminated.

The major part of the solvent is eliminated by evaporation under reduced pressure, then 25 ml of ethanol, 0.5 g of sodium hydroxide and 0.76 g of sodium borohydride are added. After stirring at ambient temperature for one hour, 50 ml of water are added, the pH is brought to 1 by the addition of a concentrated solution of hydrochloric acid, and the ethanol is evaporated under reduced pressure. The aqueous phase is alkalized by the addition of potassium hydroxide and the insoluble matter is extracted with 100 ml then two times 50 ml of toluene. The toluene phases are washed with 25 ml of water, then extracted with 50 ml of an aqueous N solution of methane sulphonic acid and 5 times 25 ml of water. The acidic aqueous phase is alkalized by the addition of a concentrated solution of ammonia and the oil which salts out is extracted with two times 50 ml then 3 times 25 ml of chloroform. The chloroformic phases are dried on magnesium sulphate and evaporated under reduced pressure. Thus, 3.57 g are obtained of N,N-dimethyl-3-[(1-aza-[2,2,2]-bicyclo-3-octyl)amino]-4-[(2-bromophenyl)thio] benzene sulphonamide. The yield, calculated relative to 1-aza-[2,2,2]-bicyclo-3-octanone or N,N-dimethyl-3-amino-4-[(2-bromophenyl)thio] benzene sulphonamide, is 72%.

EXAMPLE 3

Preparation of N,N-dimethyl-10[1-aza-[2,2,2]-bicyclo-3-octyl]-10H-2-phenothiazine sulphonamide Introduced into 10 ml of anhydrous tetrahydrofuran, placed under a dry nitrogen atmosphere, are 1.91 g of sodium amide in powder form, at ambient temperature. 1.03 g of tert-butyl alcohol and 5 ml of anhydrous tetrahydrofuran are added. The suspension is heated to 45° C. for two hours, then it is allowed to return to ambient temperature. Then, whilst stirring, a solution is added of 3.47 g of N,N-dimethyl-3-[(1-aza-[2,2,2]-bicyclo-3octyl-)amino]-4-[(2-bromophenyl)thio] benzene sulphonamide in 20 ml of tetrahydrofuran and stirring is continued for 24 hours at ambient temperature.

10 ml of water are poured into the reaction medium during cooling, and the obtained mixture is poured into 50 ml of water and 50 ml of toluene. The toluene phase is separated and the aqueous phase is extracted by two times 25 ml of toluene. The collected toluene phases are extracted by 25 ml of a normal aqueous solution of methane sulphonic acid, then by 4 times 25 ml of water. The collected aqueous phases are washed with two times 25 ml of ether, brought to pH 8 by the addition of a concentrated solution of ammonia and the insoluble matter is extracted with 4 times 50 ml of ethyl acetate. The organic phase is dried on magnesium sulphate, filtered and evaporated under reduced pressure. The obtained residue (1.51 g) is fixed on a column of silica gel and elution is effected with a mixture of 95 parts by volume of toluene and 5 parts by volume of diethylamine. Thus, 1.41 g of product are recovered which are recrystallized in 10 ml of a mixture of one part by volume of diethyl oxide and one part by volume of 2-butanone. Recrystallization provides 0.95 g of N,N-dimethyl-10[1-aza-[2,2,2]-bicyclo-3-octyl]-10H-2-phenothiazine sulphonamide. This product has a commencing melting point of 135° C., a complete melting point of 156° C., and resolidifies slowly to melt again at 183° C. (measures carried out on a Köfler bench).

EXAMPLE 4

Preparation of N,N-dimethyl-10[1-aza-[2,2,2]-bicyclo-3-octyl]-10H-2-phenothiazine sulphonamide Added to 600 ml of liquid ammonia, maintained at its boiling temperature under atmospheric pressure (approximately −30° C.) are 2.3 g of sodium and a crystal of ferric nitrate. After stirring for one hour, the dark blue solution has become a grey suspension. The suspension is cooled to −40° C. and, whilst stirring, a solution is added quickly of 12.4 g of N,N-dimethyl-3-[(1-aza-[2,2,2]-bicyclo-3-octyl)amino]-4-[(2-bromophenyl)thio] benzene sulphonamide in 60 ml of anhydrous tetrahydrofuran. Stirring is continued for 1 hour and 15 minutes at the boiling temperature of liquid ammonia, then 20 g of ammonium chloride are added and the ammonia is allowed to evaporate.

The residue is taken up by 100 ml of toluene and 100 ml of water. The mixture is stirred, the toluene phases is separated by decantation and the aqueous phase is extracted with 2 times 50 ml of toluene. The collected toluene phases are extracted with 100 ml of an aqueous N solution of methane sulphonic acid then with 5 times 50 ml of water. The collected aqueous phases are washed with 2 times 100 ml of diethyl oxide, brought to pH 8 by the addition of a concentrated solution of ammonia and the insoluble matter is extracted with 4 times 100 ml of ethyl acetate. The organic phase is dried on anhydrous magnesium sulphate, filtered and evaporated under reduced pressure. The obtained residue (9.57 g) is fixed on a column of silica gel and elution is effected with a 90/10 toluene/diethyl amine mixture. Thus, 7.4 g of product are recovered which are recrystallized in 20 ml of acetone. Recrystallization provides 6.46 g of N,N-dimethyl-10[1-aza-[2,2,2]-bicyclo-3-octyl]-10H-2-phenothiazine sulphonamide. This product has the same melting points as the one obtained in Example 3.

The yield in N,N-dimethyl-10-[1-aza-[2,2,2]-bicyclo-3-octyl]-10H-2-phenothiazine sulphonamide, calculated relative to 1-aza-[2,2,2]-bicyclo-3-octanone or N,N-dimethyl-3-amino-4-[(2-bromophenyl)thio] benzene sulphonamide, is 44%.

I claim:

1. Process for the preparation of the compound of formula:

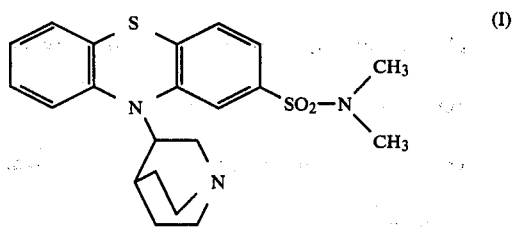

comprising the step of cyclizing the compound of formula:

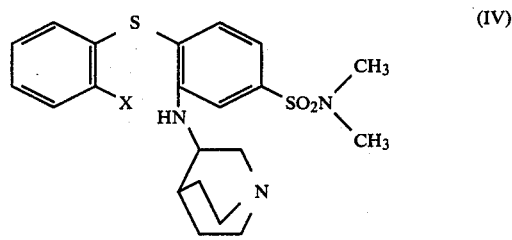

wherein X denotes a member of the group consisting of bromine and chlorine, such step being carried out in the presence of an alkali metal amide and an aprotic solvent.

2. The process according to claim 1, wherein said cyclizing step is carried out in the presence of an alcohol.

3. The process according to claim 1, wherein said cyclizing step is carried out at a temperature of between 20° C. and the boiling temperature of the solvent.

4. The process according to claim 1, wherein said cyclizing step is carried out at a temperature of between 20° C. and the boiling temperature of 1,2 dimethoxyethane.

5. The process according to claim 1, wherein said cyclizing step is carried out at an ambient temperature.

6. The process according to claim 1, wherein said cyclizing step is carried out at about 20° C.

7. The process according to claim 1, wherein the alkali metal amide is selected from the group consisting of sodium amide, lithium amide and potassium amide.

8. The process according to claim 7, wherein the alkali metal amide is sodium amide.

9. The process according to claim 1, wherein the aprotic solvent is selected from the group consisting of tetrahydrofuran, 1,2-dimethoxyethane, hexamethylphosphorous triamide, and their mixtures.

10. The process according to claim 9, wherein the aprotic solvent is tetrahydrofuran.

11. The process according to claim 2, wherein said alcohol is selected from the group consisting of tertiobutanol, monoethyl ether of diethylene glycol, and tert-amyl alcohol.

12. The process according to claim 11, wherein said alcohol is tertiobutanol.

13. The process according to claim 1, wherein X denotes bromine.

14. The process for the preparation of the compound of formula:

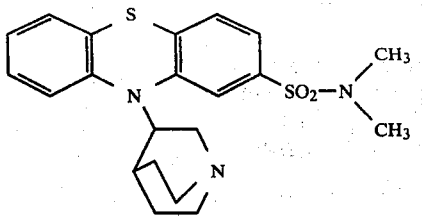
(I)

comprising the step of cyclizing the compound of formula:

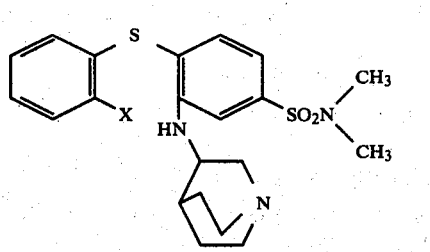
(IV)

wherein X denotes a member of the group consisting of bromine and chlorine, such step being carried out in the presence of an alkali metal amide and an aprotic solvent selected from the group consisting of tetrahydrofuran, 1,2-dimethoxyethane, hexamethylphosphorous triamide, and their mixtures, at ambient temperature in the presence of an alcohol.

15. The process according to claim 14, wherein X is bromine and said alcohol is selected from the group consisting of tertiobutanol, monoethyl ether of diethylene glycol and tert-amyl alcohol.

* * * * *